(12) United States Patent
Chapman et al.

(10) Patent No.: US 8,426,582 B1
(45) Date of Patent: Apr. 23, 2013

(54) PROCESSES FOR PREPARING CERTAIN HEXAAZAISOWURTZITANES AND THEIR USE IN PREPARING HEXANITROHEXAAZAISOWURTZITANE

(75) Inventors: Robert D. Chapman, Ridgecrest, CA (US); Richard A. Hollins, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 320 days.

(21) Appl. No.: 12/975,968

(22) Filed: Dec. 22, 2010

Related U.S. Application Data

(60) Continuation-in-part of application No. 12/022,930, filed on Jan. 30, 2008, which is a division of application No. 11/789,678, filed on Apr. 23, 2007, now Pat. No. 7,875,714.

(51) Int. Cl.
*C07D 255/00* (2006.01)
*C06B 25/34* (2006.01)

(52) U.S. Cl.
USPC .......................................... 540/554; 149/92

(58) Field of Classification Search .......... 540/554; 149/92

See application file for complete search history.

(56) References Cited

U.S. PATENT DOCUMENTS

| | | |
|---|---|---|
| 5,693,794 A | 12/1997 | Nielsen |
| 2004/0260086 A1 | 12/2004 | Cagnon et al. |

*Primary Examiner* — Brenda Coleman
(74) *Attorney, Agent, or Firm* — Charlene A. Haley

(57) ABSTRACT

A heavy-metal-free sequence leading to a superior, more economical, and scalable process for the high efficiency conversion of hexaallylhexaazaisowurtzitane (HAllylIW) to hexanitrohexaazaisowurtzitane (CL-20).

5 Claims, No Drawings

US 8,426,582 B1

PROCESSES FOR PREPARING CERTAIN HEXAAZAISOWURTZITANES AND THEIR USE IN PREPARING HEXANITROHEXAAZAISOWURTZITANE

CROSS-REFERENCE TO RELATED APPLICATIONS

This is a divisional application, claiming the benefit of, parent application Ser. No. 11/789,678 filed on Apr. 23, 2007 now U.S. Pat. No. 7,875,714, which is the parent of continuation-in-part patent application Ser. No. 12/022,930 filed Jan. 30, 2008, whereby the entire disclosures of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

One of the most important new energetic compositions for ordnance applications is hexanitrohexaazaisowurtzitane (CL-20), but its production process suffers from several economic and environmental disadvantages, mostly related to requirements for benzylamine starting material and for heavy metal (typically, palladium) catalysts. It is desirable to prepare the hexaazaisowurtzitane cage in a form that is directly nitrolyzable to CL-20 without a requirement for expensive benzylamine starting material or heavy metal catalysts. Embodiments of the invention relates to processes for preparing certain hexaazaisowurtzitanes and their use in preparing hexanitrohexaazaisowurtzitane that does not require benzylamine starting material or heavy metal catalysts, thus introducing a new, lower-cost, less wasteful, and environmentally cleaner process to produce CL-20.

BACKGROUND OF THE INVENTION

The recent publication by French researchers (Cagnon, G.; Eck, G.; Hervé, G.; Jacob, G. U.S. Patent Appl. 2004/0260086 (2004); Hervé, G.; Jacob, G.; Gallo, R. *Chem. Eur. J.* 2006, 12, 3339) that the synthesis scheme originally proposed by Nielsen (Nielsen, A. T.; Nissan, R. A.; Vanderah, D. J.; Coon, C. L.; Gilardi, R D.; George, C. F.; Flippen-Anderson, J. *J. Org. Chem.* 1990, 55, 1459) yields hexaallylhexaazaisowurtzitane (HAllylIW) provided us the opportunity to explore the potential of HAllylIW for use in new routes for the synthesis of hexanitrohexaazaisowurtzitane (CL-20). With respect to the synthesis of HAllylIW, however, it is important to note that we have confirmed that the scheme devised by Nielsen of condensation of certain primary amines with glyoxal to produce hexaazaisowurtzitane derivatives readily forms HAllylIW in solution when allylamine is condensed with glyoxal. However, under the conditions prescribed by Nielsen, no precipitate of HAllylIW is formed. We believe that the absence of such a product precipitate may have contributed to Nielsen's inability to isolate HAllylIW from the reaction of allylamine with glyoxal. This failure of HAllylIW to precipitate may have been the predominant factor contributing to Nielsen's erroneous conclusion that his efforts to extend the isowurtzitane synthesis to amines of this type were unsuccessful, notwithstanding that allylamines were expected to produce hexaazaisowurtzitanes.

SUMMARY OF THE INVENTION

Embodiments of the invention demonstrates new routes to CL-20 that meet the desired criteria of avoiding benzylamine starting material and heavy metal catalysts. It employs less expensive allylamine starting material and uses an alkali-metal strong-base catalyst. Heretofore, all synthetic routes used to prepare the hexaazaisowurtzitane cage for production of CL-20 have depended on the condensation of benzylamine with glyoxal, originally developed by Nielsen, as noted above. CL-20 has remained nearly prohibitively expensive, however (as a potential large-scale replacement for the explosive ingredient octahydro-1,3,5,7-tetranitro-1,3,5,7-tetrazocine (HMX), for example), due mainly to the high cost of benzylamine starting material and of hydrogenolysis steps involving palladium catalyst used in the debenzylation of hexabenzyl-hexaazaisowurtzitane (HBIW) intermediate in the course of preparing acylhexaazaisowurtzitane intermediates, including tetraacetyldiformylhexamisowurtzitane (TADF), tetraacetylhexaaza-isowurtzitane (TADA or TADH or TAIW), or hexaacetylhexaazaisowurtzitane (HAIW).

The by-product of hydrogenolytic debenzylation of HBIW, toluene, is not economically or cleanly reconverted to benzylamine (only via chlorination followed by amination), so benzyl is not a clean, recoverable protecting group in that system. Various researchers ((a) "Lower Cost, Improved Quality CL-20 Energetic Material"; https://www.dodmantech.com/successes/Navy/weapons/weapons_Lower-CostCL20__120805.pdf; (b) Wardle, R. B.; Hinshaw, J. C. U.S. Pat. No. 6,147,209 (2000); (c) Wardle, R. B.; Hinshaw, J. C. U.S. Pat. No. 7,129,348 (2006); and references therein) have addressed process development for reducing the cost of CL-20 production, but have not approached cost reduction by developing a fundamentally different synthetic route to the hexaazaisowurtzitane cage such as is disclosed by the present invention.

In the work disclosed here, we have applied the chemical transformation of base-catalyzed isomerization of allylamines into 1-propenylamines to known hexaallylhexaazaisowurtzitane (HAllylIW) (using potassium tert-butoxide base) to prepare a new derivative, hexa(1-propenyl)hexaazaisowurtzitane (HPIW). (This new derivative should not be confused with hexapiperonylhexaazaisowurtzitane, also designated HPIW by Tsai, H.-J. et al. *Hua Hsuch [Chemistry] (Taipei)* 2003, 61, 199.) We employed photooxygenation of HPIW by singlet oxygen—using oxygen gas photolyzed by a quartz halogen lamp in the presence of a tetraphenylporphine sensitizer—in order to oxidize some of the 1-propenyl substituents to formyl substituents. Although the oxidation reaction did not go to completion to produce hexaformylhexaazaisowurtzitane, the partially oxidized product—a polyformylhexaazaisowurtzitano—underwent nitrolysis to form CL-20 in a clean reaction. The nitrolysis of this intermediate is more efficient than direct nitrolysis of HAllylIW. Furthermore, we demonstrate that the new intermediate HPIW undergoes direct nitrolysis to form CL-20. This reactivity of the enamine HPIW is explainable as a mechanistically reasonable transformation.

DETAILED DESCRIPTION OF THE INVENTION

All synthetic routes used to prepare the hexaazaisowurtzitane cage for production of CL-20 depend on the condensation of benzylamine with glyoxal, originally developed by Nielsen, as referenced above. As noted above, CL-20 has remained nearly prohibitively expensive mainly due to the high cost of benzylamine starting material and of hydrogenolysis steps involving palladium catalyst used in the debenzylation of hexabenzylhexaazaisowurtzitane (HBIW) intermediate in the course of preparing aeylhexaazaisowurtzitane intermediates.

An alternative benzylamine-free route to a hexaacylhexaazaisowurtzitane precursor to CL-20 was envisioned following the recent report by Hervéet al. (SNPE France) of a preparation of hexaallylhexaazaisowurtzitane (HAllylIW) from allylamine and glyoxal ((a) Cagnon, G.; Eck, G.; Hervé, G.; Jacob, G. U.S. Patent Appl. 2004/0260086 (2004); (b) Hervé, G.; Jacob, G.; Gallo, R. Chem. Eur. J. 2006, 12, 3339). The new route we envisioned was to utilize HAllylIW in a well-known isomerization reaction of allylamines into 1-propenylamines. The resulting hexa(1-propenyl)hexaazaisowurtzitane could then be oxidized by singlet oxygen (which may be generated by dye-sensitized photolysis of oxygen gas, for example) via another well-known transformation: cleavage of the C=C bond of propenylamines to produce formamides (Foote, C. S.; Lin, J. W.-P. Tetrahedron Lett. 1968, 3267). The resulting hexaformylhexaazaisowurtzitane is another example of the class of hexaacylhexaazaisowurtzitanes that may be susceptible to direct nitrolysis to CL-20.

Following several failed attempts to reproduce the allylamine-glyoxal reaction according to conditions reported by Hervéet al., we were—through some process development—able to successfully recover HAllylIW by significantly modifying the isolation conditions reported by Hervéet al. (cf. Experimental Section). Thus, HAllylIW has been prepared by us in 33% yield, better than the 20-25% reported by Hervéet al.

The required rearrangement of HAllylIW was achieved (Equation 1) by base-catalyzed isomerization (Price, C. C.; Snyder, W. H. Tetrahedron Lett. 1962, 69). Clean, efficient isomerization of HAllylIW to hexa(1-propenyl)hexaazaisowurtzitane (HPIW) was effected—essentially quantitatively—by potassium t-butoxide (t-BuOK) base in dimethyl sulfoxide (DMSO) at room temperature in about 6 hours (also at 80° C. in about ¼ hour). We also demonstrated that the isomerization was efficiently achieved by introducing potassium t-butoxide as its conveniently available tetrahydrofuran solution into a solution of HAllylIW in DMSO or in dimethylformamide (DMF). Reactions in such about 1:1 solvent mixtures typically proceeded to completion in an overnight run. However, tetrahydrofuran (THF) as the sole solvent did not allow isomerization at room temperature, even on prolonged reaction. As in previous similar transformations of this type ((a) Sauer, J.; Prahl, H. Tetrahedron Lett. 1966, 2863; (b) Carisen, P. H. J.; Jorgensen, K. B. J. Heterocycl. Chem. 1997, 34, 797), the allylamine-to-propenylamine isomerizations require only catalytic t-butoxide; some of our successful runs employed ⅓ equivalent of potassium t-butoxide per allyl substituent.

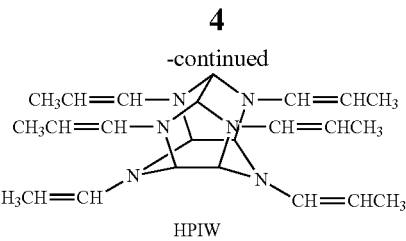

HPIW

HPIW was most easily purified (sufficiently for subsequent reactions) by removing solvent(s) under high vacuum and redissolving the HPIW in a suitable solvent in which residual potassium t-butoxide is insoluble. We initially chose benzene-$d_6$ for the sake of characterizing the dissolved HPIW and subsequent reaction products by NMR. Potassium t-butoxide has sufficiently low solubility in benzene that this is an effective purification method. However, other hydrocarbon solvents in which potassium t-butoxide has low solubility, including toluene or xylene or even some aliphatics, are suitable for this process.

From analyses of four solutions of t-butanol-potassium t-butoxide mixtures in DMSO-$d_6$—quantified by integration of the quaternary carbon absorptions vs, those of DMSO-$d_6$ (i.e., all non-protiated carbons)—linear regression of a plot of mole fraction of t-butoxide vs. quaternary carbon chemical shift produced the following relationship, useful for determining potassium t-butoxide content in DMSO-$d_6$ solutions by $^{13}$C NMR:

$$X_{t\text{-}BuO^-} = 49.17 - \delta_{13_C}^{quat}/1.36$$

This regression estimates a chemical shift of δ 66.87 for pure t-butanol in DMSO-$d_6$, comparing very favorably with a literature value of δ 66.88.

The $^1$H and $^{13}$C NMR spectra of HPIW in various solvents indicate that it exists in a few (two to four) rotational isomers (rotamers) due to cis-trans isomerism of the propenyl substitu-ents and restricted rotation about the N-propenyl bonds. Other examples of exo-heterocyclic enamines, N,N-dimethylaminomethylene-substituted pyrazoles, exhibit complex NMR spectra due to rotamers, as well (Kölle, U.; Kolb, B.; Mannschreck, A. Chem. Ber. 1980, 113, 2545).

HPIW was next subjected to oxidation by singlet oxygen, generated by halogen-lamp photolysis of oxygen gas, sensitized by catalytic amounts of zinc tetraphenylporphine (Equation 2). The transformation of enamines to formamides via photooxygenation has been reported to occur in a variety of different solvents (Foote, C. S.; Dzakpasu, A. A, Tetrahedron Lett. 1975, 1247.).

(EQ. 1)

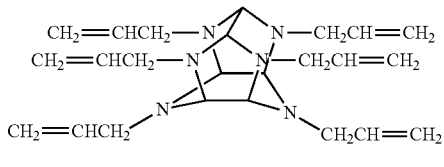

HAllylIW

| t-BuOK (cat.)
| DMSO or DMSO-THF or
| DMF-THF (Eq. 2)

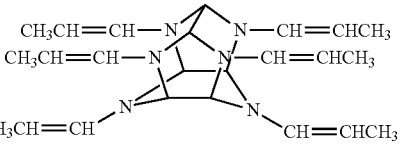

HPIW $O_2(^1\Delta_g)$ { $O_2$, hv, various solvents }

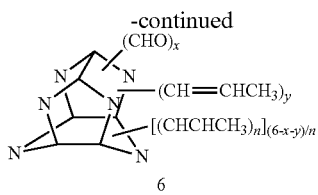

The crude oxidation product (6) is shown in Equation 2 as a hexaazaisowurtzitane cage with indeterminate numbers of formyl, 1-propenyl, and saturated polymer chain substituents and where n is indeterminate (0≦n), 0≦x≦6, 0≦y≦6, and 0≦x+y≦6. Integration of the various broad absorptions of the $^1$H NMR spectra (FIG. 1 which is shown in parent application Ser. No. 11/789,678 filed on Apr. 23, 2007) suggested that the average extent of oxidation of 1-propenyl substituents to formyl was typically between three and four substituents per hexaaza-isowurtzitane cage (i.e., x=about 3 or 4) before significant precipitation may have prevented further oxidation.

Table 1 lists the variety of conditions that were attempted to effect photooxygenation of HPIW to polyformylhexaazaisowurtzitane derivatives.

TABLE 1

Conditions of photooxygenation of HPIW

| Solvent system | Temperature | Reaction time |
| --- | --- | --- |
| $C_6D_6$ | R.T. | 3 h |
| 2:1 $C_6D_6$-acetone-$d_6$ | 0° C. | 8 h |
| 3:5 $CDCl_3$—$CD_2Cl_2$ | 0° C. | 3 h |
| 1:1 $C_6H_6$—DMSO-$d_6$ | 0° C. | 3 h |
| acetone-$d_6$ | dry ice - EtOH bath | 6 h |
| 1:5 $CD_2Cl_2$—$CDCl_3$ | dry ice - EtOH bath | 0.8 h |

The products of some photooxygenation reactions were subjected to nitrolysis after isolation from reaction suspensions by removal of all volatiles (solvent and acetaldehyde by-product). An initial run utilizing a mixture of about 98% nitric acid and acetonitrile-$d_3$ produced a minor amount of CL-20 (<10%)—confirmed by HPLC analysis as well as $^1$H and $^{13}$C NMR spectrometry—in a complex mixture after 6 days of reaction at ambient temperature. (Such prolonged reaction conditions significantly hydrolyzed acetonitrile ultimately to acetic acid.) In another run, the very viscous oily residue from a photooxygenation reaction was subjected to nitrolysis conditions using about 98% nitric acid in the presence of Nafion NR50 beads as a strong Brønsted acid catalyst (Equation 3). Nafion® resins are perfluorinated ion-exchange materials composed of carbon-fluorine backbone chains and perfluoro side chains containing sulfonic acid groups. Nafion NR50 is a polymer of the general structure:

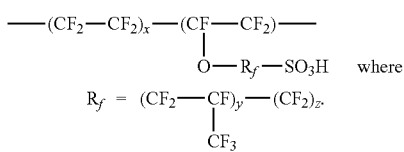

The application of Nafion® resins as versatile heterogeneous catalysts in organic transformations has been well established (Aldrich Technical Bulletin AL-163 and references therein). Other known strong Brønsted acid catalysts may be screened for efficiency in promoting this conversion, and those being efficacious will be suitable replacements for Nafion NR50.

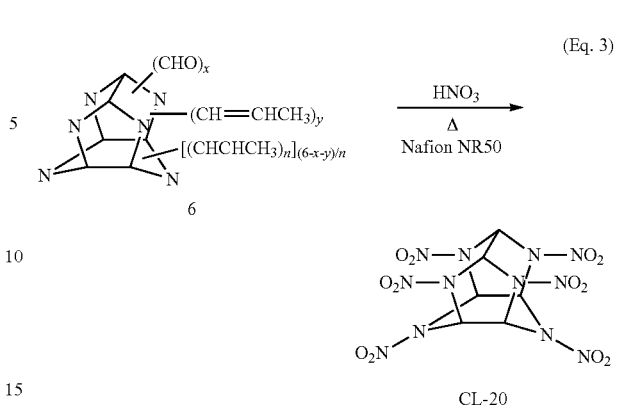

Reflux of the reaction solution for a total of about 30½ hours resulted in a surprisingly clean conversion of the crude polyformyl intermediate to CL-20. CL-20 is the predominant constituent in the spectral region attributable to hexaazaisowurtzitane species as shown by FIG. 2 which is shown in parent application Ser. No. 11/789,678 filed on Apr. 23, 2007.

In parallel with the success of the nitrolysis of a crude product (6) of photooxygenation of HPIW, an experiment to directly nitrolyze HPIW itself was carried out. Out of concern for possible hydrolysis of enamine HPIW—which could lead to disruption of the cage and degradation of intermediates—from the minor water content of the about 98% nitric acid, fuming sulfuric acid was added to nitric acid to ensure anhydrous conditions for nitrolysis. An aliquot of the reaction mixture after 4 hours' reflux, added to dichloromethane-$d_2$ for NMR analysis, showed significant CL-20 content. The mixture was not quite as clean as the nitrolysis of the photooxygenation product of HPIW, but neither had the nitrolysis reaction proceeded as long.

We have discovered that displacement of substituents on the hexaazaisowurtzitane cage is superior to nitrolysis of α-unsubstituted alkyl derivatives (example, would be formed by initial nitration of allyl substituents in HAllylIW). For example, in the reports of Herveet al. of new hexaazaisowurtzitanes, treatment of 1 g of HAllylIWwith mixed acid produced a yellow solid (whereas CL-20 is colorless or white) that contained a detectable amount of CL-20, but no yield was specified. In contrast, the isomerization disclosed here on HAllylIW produces more easily removed substituents—following their initial nitration in HPIW—and the content of CL-20 in the nitrolysis mixture is high. We speculate that transient intermediates of β-nitration of HPIW could be mixed polynitropoly(α-substituted β-nitropropyl)hexaazaisowurtzitanes (Equation 4, wherein 0≦x≦6, and X=$NO_2$, etc.). (X=H, such as with simple nitric acid, would leave α-hydroxy sites susceptible to further nitration by the nitrating reagent, still forming nitrolyzable intermediates with X=$NO_2$.)

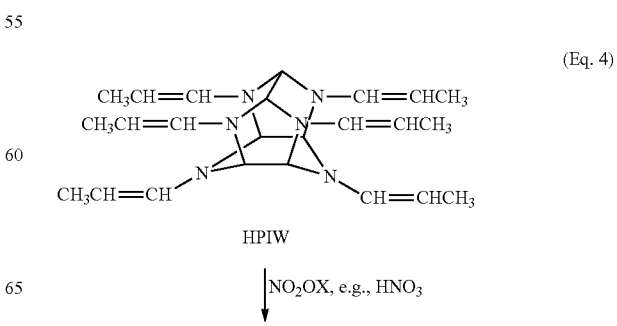

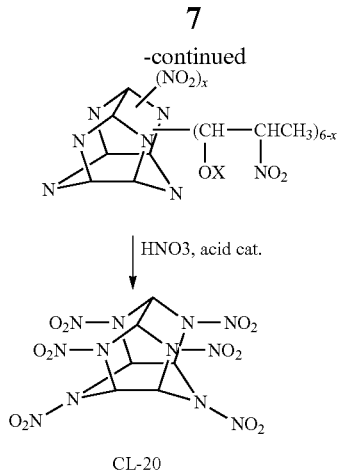

CL-20

Examples and Supporting Data

Hexa(1-propenyl)hexaazaisowurtzitane (HPIW)

Procedure A

Hexaallylhexaazaisowurtzitane (HAllylIW) was prepared as reported by Hervé et al. (following Nielsen as discussed above) with the significant modification that the product solution was basified with saturated aqueous NaHCO$_3$ and then stored at −16° C. for two days, thereby precipitating HAllylIW. The HAllylIW precipitate was filtered off and dried further by dissolving it in CH$_2$Cl$_2$, drying over MgSO$_4$, filtering, and removing the solvent. To 5 mL of a solution of 204 mg HAllylIW (0.50 mmol) in DMSO-d$_6$ was added 224 mg (2.00 mmol) of solid potassium t-butoxide. The mixture was magnetically stirred in a capped vial at ambient temperature. Progress of the isomerization was monitored occasionally by $^1$H NMR analysis of small aliquots and was seen to be complete with essentially quantitative conversion after 6 h. The $^1$H NMR (DMSO-d$_6$) spectrum of HPIW in the crude reaction mixture (FIG. 3 which is shown in parent application Ser. No. 11/789,678 filed on Apr. 23, 2007): δ 1.52-1.63 (m, CH$_3$), 4.24-4.33 (m, CHCH$_3$), 4.84 (s, 4H, cage CH), 4.89 (s, 2H, cage CH), 5.88-5.96 (NCH).

Similarly, the $^{13}$C NMR (DMSO-d$_6$) spectrum of the crude reaction mixture is shown in FIG. 4 which is shown in parent application Ser. No. 11/789,678 filed on Apr. 23, 2007: δ 11.78, 11.89, 12.20, 15.08, 74.07, 76.61, 77.14, 81.02, 82.11, 82.60, 92.75, 100.24, 100.96, 101.62, 101.77, 102.51, 134.84, 135.30, 135.46, 135.58.

HPIW was separated from residual potassium t-butoxide by pumping off DMSO-d$_6$ under high vacuum at room temperature, redissolving HPIW in about 25 mL benzene, filtering off insoluble salt (and minor possible polymeric by-products), removing benzene under vacuum at room temperature, and redissolving in CD$_2$Cl$_2$. $^1$H NMR (CD$_2$Cl$_2$): δ 1.59-1.70 (m, CH$_3$), 4.42-4.76 (m, CHCH$_3$), 4.75 (s, 4H, cage CH), 4.84 (s, 2H, cage CH), 5.93-6.02 (NCH). $^{13}$C NMR (CD$_2$Cl$_2$): δ 12.46, 12.57, 12.82, 15.49, 75.67, 75.81, 77.95, 78.30, 78.71, 78.85, 78.94, 81.92, 82.48, 83.35, 83.89, 95.45, 102.85, 103.78, 104.38, 104.87, 105.90, 135.47, 135.59, 135.76, 135.88, 136.09.

Hexa(1-propenyl)hexaazaisowurtzitane (HPIW)

Procedure B

To 1 mL of a solution of 204 mg HAllylIW (0.50 mmol) in DMSO-d$_6$ was added 1.0 mL of 1 M solution of potassium t-butoxide in tetrahydrofuran, and the mixture was magnetically stirred in a capped vial at ambient temperature. After 18 h, isomerization of HAllylIW to HPIW was complete. Again, HPIW was separated from residual potassium t-butoxide by pumping off DMSO-d$_6$ under high vacuum at room temperature, redissolving HPIW in about 25 mL benzene, filtering off insoluble salt (and minor possible polymeric by-products), removing benzene under vacuum at room temperature, and redissolving in CD$_2$Cl$_2$; and the isolated product was identical by $^1$H NMR and $^{13}$C NMR to the final product of Procedure A.

Photooxygenation of HPIW

Example

The HPIW product from an isomerization by Procedure B, following extraction into benzene and concentration, was redissolved in 6 mL of acetone-d$_6$ in a 10-mL graduated cylinder (with a standard-taper joint) fitted with a Claisen adapter to allow inlet as well as egress of an oxygen purge via a glass capillary. A few mg of zinc(II) tetraphenylporphine sensitizer was added to the solution, and the base of the cylinder was submerged in a dry ice—ethanol bath. With a purge of oxygen passing through, the solution was irradiated with a quartz halogen lamp. After 6 h of treatment, a pale pink flocculent solid was suspended in the solution. A representative sample of the suspension was withdrawn for NMR analysis after adding DMSO-d$_6$ to dissolve it (FIG. 1 which is shown in parent application Ser. No. 11/789,678 filed on Apr. 23, 2007). (Acetaldehyde by-product was clearly apparent in the $^1$H NMR spectrum of the crude mixtures.) $^1$H NMR (about 1:1 acetone-d$_6$-DMSO-d$_6$) of the hexaazaisowurtzitane product (6): δ 1.0-1.4 (bm, CH$_3$), 3.3-6.9 (bm, all CH), 8.1-8.5 (CHO). After filtration of the precipitate from acetone-d$_6$ and drying under vacuum over P$_4$O$_{10}$, the product was a pale peach colored solid.

Nitrolysis of Oxidation Product 6 to CL-20

The product suspension of a photo-oxygenation reaction of HPIW was concentrated to dryness under vacuum and pumped under high vacuum at room temperature overnight. The very viscous oily residue in a round-bottom flask—fitted with an addition funnel containing 15 mL of cold about 98% to about 100% nitric acid (Fluka "100%" nitric acid) and a nitrogen bubbler—was cooled in a dry ice-ethanol bath. The nitric acid was added quickly via the addition funnel. When the nitric acid started to freeze, the cooling bath was removed, and the organic reactant dissolved in the acid upon warming adventitiously. After reaching room temperature, the solution was heated to reflux—with a nitrogen bubbler atop the reflux condenser—in an oil bath maintained at 85-95° C. After 8½ h reflux, NMR analysis of an aliquot showed little conversion to CL-20, so several beads of Nafion NR50 were added. Reflux was resumed and continued for a total of 30½ h. An aliquot of this crude reaction solution withdrawn into acetonitrile-d$_3$ surprisingly showed, by $^1$H NMR (FIG. 2 which is shown in parent application Ser. No. 11/789,678 filed on Apr. 23, 2007), very clean conversion of all hexaazaisowurtzitane species to CL-20. By-products of nitrolysis of the substituents from 6 are also fairly simple in the spectrum. $^1$H NMR (CD$_3$CN with HNO$_3$) of crude CL-20: δ 7.81 (s, 2H), 7.91 (s, 4H).

Nitrolysis of HPIW to CL-20

Purified product solution (in benzene) from a preparation of HPIW by Procedure B was evaporated to dryness under vacuum. 10 mL CCl₄ was added, and the solution was again evaporated to dryness under vacuum. The residue in a round-bottom flask—fitted with an addition funnel containing 11 mL of cold about 98% to about 100% nitric acid (Fluka "100%" nitric acid) and a nitrogen bubbler—was cooled in a dry ice-ethanol bath. The nitric acid was added quickly via the addition funnel. When the nitric acid started to freeze, the cooling bath was removed, and the organic reactant dissolved in the acid upon warming adventitiously. After stirring while warming for 1 h, about 1 mL of 30% fuming sulfuric acid was added, and the solution was heated to reflux—with a nitrogen bubbler atop the reflux condenser—for 4 h. A sample withdrawn into dichloromethane-d₂ showed, by ¹H NMR (FIG. 5 which is shown in parent application Ser. No. 11/789,678 filed on Apr. 23, 2007), significant simplification of the hexaazaisowurtzitane region and formation of CL-20, confirmed by addition of a small amount of authentic CL-20 to the NMR sample and observation of the increase of specific peaks. ¹H NMR (CD₂Cl₂ with HNO₃, vs. trimethylsilylpropionic-d₄ acid as δ 0.00) of contained CL-20: δ 7.11 (2H), 7.45 (s, 4H).

While the invention has been described in connection with what are currently considered to be the most practical and preferred embodiments, it is to be understood that the invention is not to be limited to the disclosed embodiments, but to the contrary, is intended to cover various modifications, embodiments, and equivalent processes included within the spirit of the invention as may be suggested by the teachings herein, which are set forth in the appended claims, and which scope is to be accorded the broadest interpretation so as to encompass all such modifications, embodiments, and equivalent processes.

What is claimed is:

1. A process for preparing a compound represented by the Formula (B) comprising:

providing a compound of the structure (A)

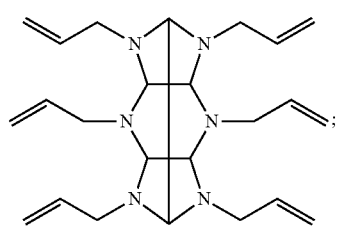

(A)

reacting the compound of structure (A) with potassium t-butoxide in the presence of dimethyl sulfoxide;

extracting a reaction product of the structure (B)

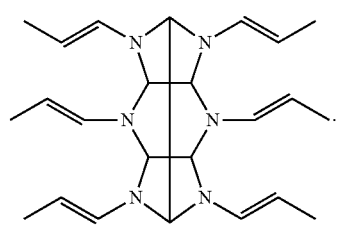

(B)

2. The process of claim 1, wherein dimethyl sulfoxide is replaced by a solution of tetrahydrofuran and dimethylformamide.

3. A process for preparing hexa(1-propenyl)hexaazaisowurtzitane comprising:

dissolving hexaallylhexaazaisowurtzitane in dimethyl sulfoxide to form a first composition;

adding potassium t-butoxide to said first composition to form a second composition;

incubating said second composition at a predetermined temperature until isomerization of hexaallylhexaazaisowurtzitane is substantially complete to form a third composition containing hexa(1-propenyl)hexaazaisowurtzitane; and, extracting hexa(1-propenyl)hexaazaisowurtzitane from said third composition.

4. The process of claim 3, wherein the potassium t-butoxide is dissolved in tetrahydrofuran before addition to said first composition.

5. The process of claim 3, wherein:

dimethyl sulfoxide is replaced by dimethylformamide; and said potassium t-butoxide is dissolved in tetrahydrofuran before addition to said first composition.

* * * * *